United States Patent [19]

Yamamoto et al.

[11] Patent Number: 4,760,078
[45] Date of Patent: Jul. 26, 1988

[54] IMMUNOMODULATOR 1,2-DITHIOL-3-THIONE DERIVATIVE COMPOSITION, USE METHOD AND PROCESS OF PRODUCING THE SAME

[75] Inventors: Itaru Yamamoto, Okayama; Akira Matsubara, Yokohama; Kanji Tomiya, Kamakura; Osamu Mizuno, Mobara; Mitsuhiro Sakaguchi, Sakaguchi; Mikio Kumakura, Mobara, all of Japan

[73] Assignee: Mitsui Toatsu Chemicals Inc., Tokyo, Japan

[21] Appl. No.: 22,349

[22] Filed: Mar. 5, 1987

[30] Foreign Application Priority Data

Mar. 5, 1986 [JP] Japan .................................. 61-46318
Jan. 30, 1987 [JP] Japan .................................. 62-18295

[51] Int. Cl.⁴ ................... A61K 31/385; C07D 339/04
[52] U.S. Cl. ...................................... 514/441; 549/36; 549/37
[58] Field of Search ..................... 549/36, 37; 514/441

[56] References Cited

U.S. PATENT DOCUMENTS 3,364,232 1/1968 Anderson .............................. 549/36
4,382,816 5/1983 Bahr ..................................... 549/37

Primary Examiner—Mary C. Lee
Assistant Examiner—J. G. Mullins
Attorney, Agent, or Firm—Birch, Stewart, Kolasch & Birch

[57] ABSTRACT

A novel 1,2-dithiol-3-thione derivative which has an immunomodulating property, which is expressed by the formula (I):

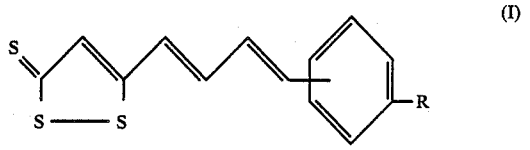

wherein R denotes hydrogen, halogen, lower alkoxy group, lower alkyl group, amino group, lower alkyl-substituted amino group or lower alkoxycarbonyl group.

16 Claims, No Drawings

IMMUNOMODULATOR 1,2-DITHIOL-3-THIONE DERIVATIVE COMPOSITION, USE METHOD AND PROCESS OF PRODUCING THE SAME

BACKGROUND OF THE INVENTION

I. Field of the Invention

This invention relates to a novel 1,2-dithiol-3-thione derivative having an immunomodulating property, to a process of producing the same, and to an immunomodulator composition comprising the same as an effective ingredient.

II. Description of the Prior Art

Immunomodulating action is understood as an action which scarcely influences an organism when the immune system of the organism is normally functioning, but which stimulates the immune system of the organism when the immune system is weakened, and which suppresses the immune system when it is hyperactive.

Hyperactivity of the immune system may be caused by the hypoactivity of immunosuppressive mechanism, while conversely, the hypoactivity of the immune system may be caused by the hyperactivity of the immunosuppressive mechanism. Thus, immunomodulation regulatively controls the fractuation of the immunosuppressive power of the immunosuppressive mechanism to normalize the mechanism.

Conventional immunomodulators such as levamisole and thymus hormones are reported to have a number of side effects when they are used clinically.

For example, levamisole is reported to have side effects such as vomiturition, eruption and hemotoxicity, as well as the most serious side effect of granulocytopenia. Although granulocytopenia is a side effect which disappears upon stopping the administration of levamisole, when it is continuously administered for a long time, the number of leucocytes must be strictly monitored.

Thus, an immunomodulator which does not have serious side effects is strongly demanded.

Recently, the necessity of an immunomodulator which prohibits the in vivo infection and growing of pathogenic parasites such as viruses and bacteria, while also strengthening the resistivity against endogenous alien matter such as cancer cells, is prominently increasing. Further, it is desired that such an immunomodulator also be used for curing various allergies, rheumatic arthritis, diabetes, immunodeficiency syndrome, multiple sclerosis and Guillain-Barre syndrome.

The present inventors have found that lipoic acid (DL-thioctic acid), which is widely used for curing hepatopathy, has an excellent immunomodulating effect, and published the discovery (Proceedings of Pharmaceutical Society of Japan, 104th Annual Meeting, p. 397 (1984)).

SUMMARY OF THE INVENTION

The object of the present invention is to provide an immunomodulator having a stronger immunomodulating effect than those of conventional immunomodulators, and which does not have a serious side effect.

The present inventors have found that a novel 1,2-dithiol-3-thione derivative is very safe for use, and has an even stronger immunomodulating effect than lipoic acid to complete the present invention.

Thus, the present invention provides a 1,2-dithiol-3-thione derivative of the formula (I):

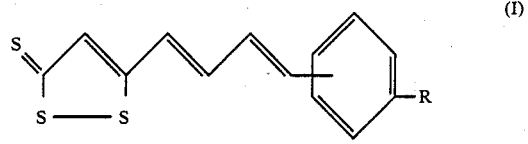

wherein R denotes hydrogen, halogen, lower alkoxy group, lower alkyl group, amino group, lower alkyl-substituted amino group or lower alkoxycarbonyl group.

The immunomodulator of the present invention which comprises as an effective ingredient the compound of the formula (I) may widely be used for curing autoimmune diseases including chronic rheumatic arthritis, systemic lupus erythematosus, nephritis, diabetes, immunodeficiency, multiple sclerosis, Guillant-Barre syndrome; direct and deferred allergies; and immunodeficiencies including malignant tumor and severe infectious diseases.

DETAILED DESCRIPTION OF THE PREFERRED EMBODIMENTS

In the above-described formula (I), the term "lower" means methyl, ethyl, propyl and butyl, as well as its structural isomers such as isopropyl, isobutyl and tertiarybutyl.

Among the compounds of the formula (I), preferred compounds include 5-(4-phenyl-1,3-butadienyl)-1,2-dithiol-3-thione, 5-4-(4-chlorophenyl)-1,3-butadienyl-1,2-dithiol-3-thione, 5-{4-(4-methoxyphenyl)-1,3-butadienyl}-1,2-dithiol-3-thione, 5-{4-(p-toluyl)-1,3-butadienyl}-1,2-dithiol-3-thione, 5-{4-(o-chlorophenyl)-1,3-butadienyl}-1,2-dithiol-3-thione, and 5-{4-(m-methylphenyl)-1,3-butadienyl}-1,2-dithiol-3-thione The immunomodulator composition of the present invention contains the above-described novel compound of formula (I) in a conventional pharmaceutically acceptable carrier or diluent, and may be formulated as tablets, capsules, powder and granules for oral administration, and also may be formulated as injections and suppositories. The dose of administration may be 0.1 to 500 mg per each administration. The administration may usually be conducted once a day, but may be conducted two or more times depending on the condition of the patient.

The novel 1,2-dithiol-3-thione derivative of the present invention may be produced by condensing a cinnamaldehyde derivative of the formula (II):

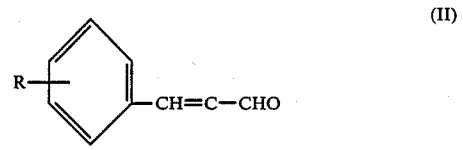

(wherein R denotes hydrogen, halogen, lower alkoxy group, lower alkyl group, amino group, lower alkyl-substituted amino group or lower alkoxycarbonyl group) with 5-methyl-1,2-dithiol-3-thione in an organic solvent in the presence of a base.

Aliphatic and aromatic hydrocarbons, halogenated hydrocarbons, alcohols and ethers may be used as the organic solvent in this process. Preferred examples of the organic solvent include hexane, toluene and methanol.

Preferred examples of the base include lower alkoxides of alkali metals and alkaline earth metals; and organic bases such as triethyl amines and 1,8-diazabicyclo-5,4,0-undec-7-ene (DBU). The amount of the base used in this process is 1 to 10 equivalents, preferably 2 to 5 equivalents with respect to the 5-methyl-1,2-dithiol-3-thione.

The process may be conducted at a temperature of $-10°$ C. to 100° C., and preferably 0° C. to 50° C. The reaction completes in about 1 hour with agitation of the reaction medium.

The production of the novel 1,2-dithiol-3-thione derivative by the condensation of an aliphatic aldehyde derivative and 5-methyl-1,2-dithiol-3-thione is believed to be novel.

The present invention will now be described with reference to the preferred examples thereof. It should be noted that these examples are presented for the purpose of illustration only, and they should not be interpreted as restrictive in any way. In the examples, the starting material 5-methyl-1,2-dithiol-3-thione was prepared in accordance with the teachings by Thurllier, A., Bull. Soc. Chim. France (1962), p. 2182, as described in the Reference Examples 1 and 2 below.

REFERENCE EXAMPLE 1

4,4-di(methylmercapto)-3-butene-2-one

In 500 ml of anhydrous benzene, 40 g (1.0 mol) of 60% sodium hydride was suspended. Keeping the temperature of the suspension not higher than 60° C., 88.2 g (1.0 mol) of t-amylalcohol was added dropwise to the suspension.

Then the mixture was heated to reflux under agitation for 2 hours, and left to stand at room temperature overnight. Keeping the temperature of the mixture not higher than 10° C., a mixture of 29 g (0.5 mol) acetone and 38.1 g (0.5 mol) of carbon disulfide was added dropwise. After stirring the reaction mixture at room temperature for 5 hours, 141.9 g (1.0 mol) of methyl iodide was added dropwise with stirring while cooling the mixture in ice water. After stirring at room temperature for 3 hours, the mixture was left to stand overnight.

Water was added to the reaction mixture and an organic phase was separated. After washing the organic phase with water, it was dried over magnesium sulfate. Solvent was evaporated under reduced pressure and hexane was added to the residue to crystallize it to obtain crude crystals of 59.7 g. By recrystallizing the crude crystals from ethanol, yellow needle-like crystals of 4,4-di(methylmercapto)-3-butene-2-one were obtained.

Yield: 51.9 g (61.4%).
Melting Point: 65°–66.5° C.

REFERENCE EXAMPLE 2

5-methyl-1,2-dithiol-3-thione

In 1.3 liters of xylene, was suspended 130 g (0.58 mol) of phosphorus pentasulfide and 51.9 g (0.32 mol) of 4,4-di(methylmercapto)-3-buthene-2-one in 200 ml of xylene was added dropwise under reflux. After heating to reflux for 30 minutes, the reaction mixture was poured into 1.5 liters of diethyl ether. Insolubles were removed by filtration, and the mother liquor was washed with water, and then with a 1% aqueous solution of sodium hydroxide. The organic phase was dried over magnesium sulfate, and the solvent was evaporated under reduced pressure. The residue was purified by silica gel chromatography (hexane:ethyl acetate=10:1) to obtain a red oil of 5-methyl-1,2-dithiol-3-thione.

Yield: 21.9 g (46.0%).
NMR (CDCl$_3$, $\delta_{ppm}$) 7.0 (1H, S) 2.54 (3H, S).

EXAMPLE 1

5-(4-phenyl-1,3-butadienyl)-1,2-dithiol-3-thione (Compound No. 1)

To 40 ml of methanol, 600 mg (24 milligrams atom) of magnesium metal was added, and the mixture was heated to reflux for 1 hour to dissolve the magnesium metal. While cooling the mixture in ice water, 1.4 g (10 milli moles) of cinnamaldehyde, and then 1.56 g (10 milli moles) of 5-methyl-1,2-dithiol-3-thione were added to the mixture and the mixture was stirred for 1 hour at the same temperature. Separated crystals were recovered by filtration, and were added to 300 ml of ethyl acetate. Insolubles were removed by filtration, and the mother liquor was washed with water and dried over magnesium sulfate. The solvent was evaporated under reduced pressure, and the obtained crude crystals were recrystallized from benzene-ethanol to obtain dark red crystals of
5-(4-phenyl-1,3-butadienyl)-1,2-dithiol-3-thione.

Yield: 0.53 g (19.2%).
Melting Point: 160°–161° C.
NMR (DMSO-d$_6$, $\delta_{ppm}$) 7.3–7.7 (5H, m) 6.8–7.28 (5H, m).

In the same manner as in Example 1, a corresponding cinnamaldehyde derivative (i.e., 4-chloro-cinnamaldehyde, 4-methoxy-cinnamaldehyde, 4-dimethylamino-cinnamaldehyde, p-methyl-cinnamaldehyde, o-chloro-cinnamaldehyde or m-methyl-cinnamaldehyde) was reacted with 5-methyl-1,2-dithiol-3-thione to prepare the following compounds.

5-{4-(4-chlorophenyl)-1,3-butadienyl}-1,2-dithiol-3-thione (Compound No. 2)
Appearance: Red Crystal
Yield: 18.9%
Melting Point: 144°–145° C.
NMR (DMSO-d$_6$, $\delta_{ppm}$) 6.80–7.25 (4H, m) 7.30–7.79 (5H, m).

5-{4-(4-methoxyphenyl)-1,3-butadienyl}-1,2-dithiol-3-thione (Compound No. 3)
Appearance: Black Crystal.
Yield: 13.6%
Melting Point: 147°–148° C.
NMR (DMSO-d$_6$, $\delta_{ppm}$) 7.28–7.69 (4H, m) 6.78–7.12 (5H, m) 3.79 (3H, s).

5-{4-(4-dimethylaminophenyl)-1,3-butadienyl}-1,2-dithiol-3-thione (Compound No. 4).
Appearance: Dark Green Crystal.
Yield: 5.3%
Melting Point: 133°–134° C.

5-{4-(p-toluyl)-1,3-butadienyl}-1,2-dithiol-3-thione (Compound No. 5)
Appearance: Dark Green Crystal.
Yield: 26.7%.
Melting Point: 144°–145° C.
NMR (CDCl$_3$, $\delta_{ppm}$) 2.44 (3H, s) 6.50–7.50 (9H, m).
Elemental Analysis (C$_{14}$H$_{12}$S$_3$): Calc.: C; 60.83, H; 4.38, S; 34.79, Anal.: C; 60.73, H; 4.11, S; 35.05.

5-{4-(o-chlorophenyl)-1,3-butadienyl}-1,2-dithiol-3-thione (Compound No. 6)

Appearance: Dark Red Crystal.
Yield: 11.0%.
Melting Point: 161°–162° C.
NMR (DMSO-d$_6$, $\delta_{ppm}$) 7.87 (1H, s) 6.84–7.70 (8H, m).

5-{4-(m-methylphenyl)-1,3-butadienyl}1,2-dithiol-3-thione (Compound No. 7)
Appearance: Dark Red Crystals.
Yield: 23.1%
Melting Point: 143.5°–144.5° C.
NMR (DMSO-d$_6$, $\delta_{ppm}$) 2.36 (3H, s) 6.95–7.51 (9H, m).

The test results and an example of the formulation of the compound of the present invention will now be described concretely.

Test 1
Action Against Blast Formation Reaction of Mouse Spleen Cells

The action of the compound of the present invention against the DNA synthesis of mouse spleen cells, which synthesis is induced by Concanavalin A (hereinafter referred to as ConA for short) was examined.

$1\times10^5$ spleen cells of BALB/C mouse (female, 10 weeks old) were incubated with 2 $\mu$g/ml of ConA and $10^{-6}$, $10^{-5}$, or $10^{-4}$M of the compound of the present invention in RPMI 1640 medium containing 10% bovine serum albumin at 37° C. in an atmosphere containing 5% CO$_2$ for 48 hours. Subsequently, $^3$H-thymidine was added to the culture and then the culture was incubated for another 18 hours.

The incubated cells were collected with a harvester and the intake of $^3$H-thymidine by the cells was determined using a scintillation counter.

The results are shown in Table 1. The activity in the table is relative activity when the activity of the control is 100.

TABLE 1

| Experiment | Compound | Concentration (M) | Activity |
|---|---|---|---|
| 1 | Control | — | 100 |
|  | Compound 1 | $10^{-6}$ | 250 |
|  |  | $10^{-5}$ | 281 |
|  |  | $10^{-4}$ | 196 |
|  | Compound 3 | $10^{-6}$ | 175 |
|  |  | $10^{-5}$ | 338 |
|  |  | $10^{-4}$ | 291 |
|  | Lipoic Acid | $10^{-6}$ | 142 |
|  |  | $10^{-5}$ | 146 |
|  |  | $10^{-4}$ | 234 |
| 2 | Control | — | 100 |
|  | Compound 5 | $10^{-6}$ | 130 |
|  |  | $10^{-5}$ | 228 |
|  | Lipoic Acid | $10^{-6}$ | 95 |
|  |  | $10^{-5}$ | 159 |

Test 2
Antibody Production-Promoting Action

The action of the compound of the present invention with respect to the antibody production of mouse against sheep red blood cells (SRBC) was examined.

To tail veins of ICR mice (female, 7 weeks old, 4 mice in each group), $5\times10^7$ SRBC were injected to immunize the mice. The compound of the present invention suspended in 0.5% methyl cellulose solution was orally administered twice to the mice on the day of immunization and on the next day. Three days after immunization, the number of spleen cells producing anti-SRBC antibody (PFC number) was checked by Jerne's method (Science Vol. 140, p. 405 (1963)).

The results are shown in Table 2. In Table 2, the activity is the relative PFC number when the PFC number of the control is 100.

TABLE 2

| Compound | Administration Dose (mg/kg) | Activity |
|---|---|---|
| Control | — | 100 |
| Compound 1 | 0.4 | 258 |
|  | 2.0 | 149 |
| Compound 3 | 0.4 | 117 |
|  | 2.0 | 186 |

Test 3
Action Against Experimental Allergic Encephalomyelitis (EAE) of Rats

Chronic recurrent rat EAE which is a model of autoimmune diseases such as multiple screlosis was prepared according to Feuer's method, and the action of the compound of the present invention against rat EAE was examined.

To both rear foot pads of each Lewis rat (female, 7 weeks old, 8 rats per group), 0.2 ml of emulsion consisting of 10 mg of lyophilized spinal cord and Freund's complete adjuvant (containing 2 mg of tubercule bacillus H37RA strain) was dividedly inoculated.

The compound of the present invention was suspended in 0.5% methyl cellulose solution and the suspension was subcutaneously administered 8 times to the rats from 7 days prior to the inoculation to 7 days after the inoculation. The clinical states of the rat were observed until 50 days after the inoculation, and were given scores of 0 to 5 according to the Feuer's method. Survival rate of the rats after 50 days from the inoculation was also checked.

The results are shown in Table 3. As can be seen from the mean score obtained when the rats were alive, the Compound 1 of the present invention showed excellent inhibition against rat EAE.

TABLE 3

| Compound | Dose mg/kg/d | Crisis Day (Mean) | Clin. Score (Mean) | Survival Rate |
|---|---|---|---|---|
| Control | — | 9.1 ± 0.6 | 1.0 ± 0.4 | 6/8 |
| Compound 1 | 0.3 | 10.5 ± 0.9 | 0.3 ± 0.1* | 8/8 |
|  | 3 | 10.3 ± 0.7 | 0.2 ± 0.1* | 8/8 |

Mean Standard Deviation p < 0.01

Test 4
Acute Toxicity

Oral toxicity of the compound of the present invention was examined using mice.

The compound of the present invention was suspended in 0.5% solution of methyl cellulose and the suspension was orally administered to ddY mice (male, 7 weeks old, 6 mice per group). The conditions of the mice were observed and the number of deaths in 14 days from administration was checked. In the case where 500 mg/kg of Compound 1 was administered, there were no deaths and the body weight of the mice was not influenced. On the other hand, one mouse in 6 mice died when 300 mg/kg of lipoic acid was administered.

EXAMPLE OF FORMULATION (TABLETS)

Tablets having the following composition containing 20 mg of the active ingredient were prepared by a conventional method.

| | |
|---|---|
| Compound 1 | 20 mg |
| Lactose | 78 mg |
| Corn Starch | 50 mg |
| Magnesium Stearate | 2 mg |

Other compounds of the present invention were also able to be tabletted in the same way.

We claim:

1. A 1,2-dithiol-3-thione derivative of the formula (I):

wherein R denotes hydrogen, halogen, lower alkoxy group, lower alkyl group, amino group, lower alkyl-substituted amino group or lower alkoxycarbonyl group.

2. The derivative of claim 1, which is 5-(4-phenyl-1,3-butadienyl)-1,2-dithiol-3-thione, 5-{4-(4-chlorophenyl)-1,3-butadienyl}-1,2-dithiol-3-thione, 5-{4-(4-methoxyphenyl)-1,3-butadienyl}-1,2-dithiol-3-thione, 5-{4-(p-toluyl)-1,3-butadienyl}-1,2-dithiol-3-thione, 5-{4-(o-chlorophenyl)-1,3-butadienyl}-1,2-dithiol-3-thione, or 5-{4-(m-methylphenyl)-1,3-butadienyl}-1,2-dithiol-3-thione.

3. The derivative of claim 1, which is 5-(4-phenyl-1,3-butadienyl)-1,2-dithiol-3-thione.

4. The derivative of claim 1, which is 5-{4-(4-chlorophenyl)-1,3-butadienyl}-1,2-dithiol-3-thione.

5. The derivative of claim 1, which is 5-{4-(4-methoxyphenyl)-1,3-butadienyl}-1,2-dithiol-3-thione.

6. The derivative of claim 1, which is 5-{4-(p-toluyl)-1,3-butadienyl}-1,2-dithiol-3-thione.

7. The derivative of claim 1, which is 5-{4-(o-chlorophenyl)-1,3-butadienyl}-1,2-dithiol-3-thione.

8. The derivative of claim 1, which is 5-{4-(m-methylphenyl)-1,3-butadienyl}-1,2-dithiol-3-thione.

9. An immunomodulator composition comprising: an effective immunomodulating amount of the 1,2-dithiol-3-thione derivative of the formula (I) as defined in claim 1; and a pharmaceutically acceptable carrier.

10. The composition of claim 9, in the form of a solution.

11. The composition of claim 9, in the form of a tablet.

12. A method for treating an immune system disorder comprising: administering to a patient having an immune system disorder an effective immunomodulating amount of the composition of claim 9.

13. The method of claim 12, wherein said composition is administered orally.

14. The method of claim 12, wherein said composition is administered by injection.

15. The method of claim 12, wherein said 1,2-dithiol-3-thione derivative of the formula (I) is administered in a dose of 0.1 to 500 mg.

16. A process of producing a 1,2-dithiol-3-thione derivative of the formula (I), comprising the step of condensing an aliphatic aldehyde compound of the formula (II):

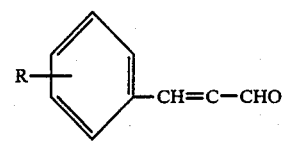

wherein R denotes hydrogen, halogen, lower alkoxy group, lower alkyl group, amino group, lower alkyl-substituted amino group or lower alkoxycarbonyl group with 5-methyl-1,2-dithiol-3-thione in an organic solvent in the presence of a base.

* * * * *